United States Patent [19]

Boyle et al.

[11] Patent Number: 5,237,050

[45] Date of Patent: Aug. 17, 1993

[54] BACTERIAL PLASMIN RECEPTORS AS FIBRINOLYTIC AGENTS

[75] Inventors: Michael D. P. Boyle, Whitehouse, Ohio; Richard Lottenberg, Gainesville, Fla.; Christopher Broder, Rockville, Md.; Gregory Von Mering, Gainesville, Fla.

[73] Assignee: University of Florida Research Foundation, Inc., Alachua, Fla.

[21] Appl. No.: 524,411

[22] Filed: May 15, 1990

Related U.S. Application Data

[63] Continuation-in-part of Ser. No. 330,849, Mar. 29, 1989, abandoned.

[51] Int. Cl.$^5$ .................. C07K 15/00; A61K 39/00
[52] U.S. Cl. ...................... 530/350; 530/825; 530/402; 530/388.25; 530/381
[58] Field of Search ............ 530/810, 825, 350; 435/174; 424/94.64

[56] References Cited

PUBLICATIONS

Sevilla et al. BBRC 130(1): 91. 1985.
Broeseker et al (Microb. Pathog 5(1):19. 1988) CIAS Abstract 110:55244.
Broder et al. JBC 266(8): 4922. 1991.
Broder, C. C. Dissentation Abstracts 51/03-B: p. 1105. 1989.
Lotteoberg et al Infection and Immunity 55(8): pp. 1914–1928. 1987.
Sevilla et al. BBRC 130(1): 91. 1985.

*Primary Examiner*—Elizabeth C. Weimar
*Assistant Examiner*—Suzanne Ziska
*Attorney, Agent, or Firm*—Saliwanchik & Saliwanchik

[57] ABSTRACT

The subject invention concerns novel methods and compositions for thrombolytic therapy. More specifically, a receptor with high affinity for plasmin has been characterized, purified, cloned, and expressed. This receptor can be used in combination therapies where it is administered prior to, concurrently with, or after a plasminogen activator. Also, this receptor can be bound to plasmin and administered to humans or animals in need of fibrinolytic activity. Additionally, the invention pertains to a novel immobilized form of plasmin which advantageously accumulates at the point where antifibrinolytic activity is needed.

3 Claims, No Drawings

BACTERIAL PLASMIN RECEPTORS AS FIBRINOLYTIC AGENTS

CROSS-REFERENCE TO A RELATED APPLICATION

This is a continuation-in-part of our copending U.S. application Ser. No. 330,849, filed on Mar. 29, 1989, abandoned Oct. 15, 1990.

BACKGROUND OF THE INVENTION

Ten years ago, the food and drug administration first approved the use of plasminogen activators for thrombolytic therapy. It was originally recommended for the treatment of deep-vein thrombosis and serious pulmonary embolisms. This approach is now also used for treating acute peripheral arterial thrombosis and acute coronary thrombosis and for solubilizing clots in catheters and shunts.

With the development of recombinant DNA technology and the cloning and expression of tissue plasminogen activator (TPA), we have now entered a new age for thrombolytic agents with unique physiological properties and therapeutic promise. The original plasminogen activators that have been used clinically were streptokinase and urokinase. These agents produced in the patients a generalized lytic state which had a variety of side effects that were not directly targeted at solubilizing the fibrin clot. Tissue plasminogen activator, because of its fibrin binding capacity, enhances the selectivity of these agents for fibrin degradation. It is thus being greeted with great fanfare as the new generation of fibrinolytic agents.

Tissue plasminogen activator is not without its potential side effects, and, furthermore, its cost is prohibitive for use in many settings. For example, the V.A. in Gainesville will not authorize tissue plasminogen activator therapy over streptokinase therapy because of its enormous cost. Furthermore, the application of this fibrinolytic therapy to domestic animals or food production animals is limited by the enormous cost.

It is clear to most experts that the wonder drug nature of tissue plasminogen activator has been highly overrated. TPA has been found to have a very short half life in the body. Also, pharmacological doses of tissue plasminogen activator produce a significant bleeding risk for the patient, and in the case of coronary artery thrombosis, re-occlusion of the blood vessel following successful clot lysis occurs in a significant number of patients. The need for an inexpensive, and perhaps even better form of treatment is clearly evident. The use of combination therapies whereby existing compositions and methods are integrally linked in novel ways with new materials and procedures could enhance the effectiveness of plasminogen activators and possibly reduce the amount of plasminogen activator needed to achieve the desired results.

Recently, we have described in our laboratory the presence of a selective, high affinity receptor for human plasmin and other species of plasmin on the surface of certain group A streptococci (Lottenberg, R., C. C. Broder, M. D. P. Boyle [1987] Infect. Immun. 55:1914–1918). This receptor binds plasmin with a very high affinity and a very slow off-rate. Once bound, the enzyme retains its enzymatic activity and cannot be regulated by the natural physiological regulator of plasmin $\alpha 2$ antiplasmin. This means that bacteria with plasmin bound to their surfaces are potent, non-regulatable fibrinolytic agents.

BRIEF SUMMARY OF THE INVENTION

The subject application pertains to novel compositions and methods for thrombolytic therapy. A receptor for human plasmin has been identified, purified, characterized, cloned and expressed. This receptor has been found to bind with very high affinity to plasmin. When bound to the receptor, plasmin retains its enzymatic activity but is not regulated by $\alpha 2$ antiplasmin. The isolation and purification of the plasmin receptor protein makes it possible to administer novel compositions and treatments to achieve fibrinolytic activity. Specifically, the receptor protein can be used in combination with existing plasminogen activators in ways which enhance the usefulness of the plasminogen activators while minimizing the negative aspects of these agents. For example, by concurrent or sequential administration of plasminogen activators and the receptor protein it is possible to prolong the effects of the plasminogen activator. The prolongation results from the binding of the receptor molecule to free plasmin produced by the activity of the plasminogen activator. Once the receptor binds with high affinity to the plasmin, the plasmin is no longer inhibited by $\alpha 2$ antiplasmin. In this fashion, the amount of plasminogen activator needed to achieve the desired plasmin activity can be reduced and the disadvantageous effects of the short half life of the plasminogen activator can be minimized. The immobilized or receptor-bound plasmin can be used in conjunction with the administration of streptokinase, urokinase, tissue plasminogen activator, or other plasminogen activators. The use of our novel plasmin constructs in such a treatment regimen could help to prevent re-occlusion of blood vessels, while the reduced concentration of the plasminogen activator lowers the risk of bleeding.

Furthermore, the receptor molecule can be conjugated to a monoclonal antibody specific for fibrin. In this way, the plasmin can be targeted to the fibrin clot where the fibrinolytic activity is needed. Also, this will help to reduce the amount of plasmin circulating freely in the blood system.

In another embodiment of the subject invention, plasmin can be bound to the receptor before administration to the human or animal in need of thrombolytic activity. Plasmin bound to the receptor will supply the fibrinolytic activity without being rapidly inhibited by $\alpha 2$ antiplasmin.

The subject invention further concerns a process which comprises treating a human or animal in need of fibrinolytic activity with bacteria comprising a selective, high affinity receptor for plasmin, human nad otherwise. Exemplified herein is the use of a group A streptococcus receptor which binds human plasmin with, advantageously, a very high affinity and a very slow off-rate. This form of immobilized plasmin has a number of potential applications for thrombolytic therapy, not only in man, but also in animals.

The plasmin receptor used according to the subject invention can be purified from certain bacteria as described below. Also, the receptor can be produced by recombinant techniques using novel clones which express the receptor. The purified receptor is a $Mr \approx 41,000$ dalton protein that is distinct from the $Mr \approx 48,000$ streptokinase molecule produced by the same bacteria. Unlike the streptokinase, the plasmin receptor protein lacks plasminogen activator activity.

DETAILED DESCRIPTION OF THE INVENTION

One of the major problems with plasminogen activator administration is the lytic state that accompanies injection of high concentrations of streptokinase or, to a lesser degree, tissue plasminogen activator. This is due to the generation of plasmin from the plasminogen as the activators circulate throughout the human or animal. Tissue plasminogen activator has a certain affinity for fibrin that allows activation to occur preferentially in the region of the clot.

The purified plasmin receptor of the subject invention can be used in combination with plasminogen activators to produce the desired thrombolytic activity. Advantageously, the use of plasmin receptors could reduce the amount of plasminogen activator needed to achieve the necessary activity. By binding with plasmin generated by plasminogen activators, the receptor is able to greatly prolong the effect of the plasminogen activator. The adverse effects of the short half-life of plasminogen activators are thereby minimized. When the receptor binds to plasmin, the plasmin retains its enzymatic activity but is not inhibited by $\alpha 2$ antiplasmin. Also, the receptor can be conjugated to antibodies which serve to target the enzymatic activity of the plasmin to the blood clot where activity is needed. The use of this combined therapy of plasminogen activator and plasmin receptor facilitates a much more efficient treatment for blood clots. The combined therapy minimizes the deleterious effects which accompany current thrombolytic therapies.

An alternate form of therapy involves the administration of plasmin already bound to the receptor. The receptor may be purified or still associated with the bacteria surface. Plasmin associated with a bacteria circulates freely in the bloodstream until cleared by the reticuloendothelial system and, by virtue of its particle size, it can accumulate in areas where blood clots have formed. Once there, the bacterium-bound enzyme can degrade the fibrin and clear the clot. The bacteria then continue to circulate until the reticuloendothelial system clears the organisms. Our findings that the plasmin receptor is extremely stable and is present on non-viable bacteria makes this approach particularly attractive. It enables micromolar quantities of plasmin to be immobilized on bacteria by adsorption. The bacterial bound plasmin can then be administered intravenously without significant toxicity. The organisms, being non-viable, do not present any risk to the human or animal patient, and the potential for clearance of teh oirganisms following a reasonable half-life in the plasma, would be anticipated by virtue of the normal reticuloendothelial cell function of the human or animal.

Although a pathogenic group A streptococcus is exemplified herein, plasmin receptors have also been identified on a number of other organisms including isolates that, even when viable, are not human pathogens. Other organisms which can be used to practice the subject invention include other groups of streptococci including B, C and G. Also, bovine *Pasteurella haemolytica* as well as *Staphylococcus aureus* microorganisms can be used. These orgaisms are well-known in the art and are illustrative, but not exhaustive, of the microorganisms which come within the scope of the subject invention.

The major advantage of using plasmin bound to bacteria is the ability to produce a fibrinolytic agent that has selectivity towards the clot, and would not result in a widespread lytic state, all of which can be achieved at a very moderate cost. In addition, the bacterial plasmin receptor has been shown to bind not only to human but other species of plasmin, thereby enabling this approach to thrombolytic therapy to be extended to domestic and food producing animals.

Of particular interest in this regard is a major economic disease in cattle which involves fibrin pneumonia that occurs in cows infected with *Pasteurella haemolytica*. This is a major killer of animals, particularly those suffering from immunosuppression as a consequence of viral infection. This is particularly important in feed lots and under conditions where large numbers of cattle are housed together. There is a great need for the ability to treat the fibrin deposits in the lung, which ultimately suffocate the animal, by aerosol treatment with a plasmin-bacterial complex. In addition, situations for which thrombolytic therapy has been used in human medicine could now be applied to similar situations in animals.

Among the advantages of using bacteria coated with plasmin, are (1) the increased selectivity achieved by immobilizing plasmin in a non-regulatable form on a particle that would circulate with a predictable half-life in the serum of an individual animal; and (2) the low cost, which would then enable the approach to be used for animals as well as man.

Following are examples which illustrate procedures, including the best mode for practicing the invention. These examples should not be construed as limiting. All percentages are by weight and all solvent mixture proportions are by volume unless otherwise noted.

EXAMPLE 1

Human plasminogen

Plasminogen was prepared from human plasma by chromatography on lysine sepharose (Sigma Chem. Co., St. Louis, Mo., U.S.A.) and molecular sieving chromatography on Sephadex G-100 (Lottenberg, R., F. R. Dolly, C. S. Kitchens [1985] Am. J. Hematol. 19:181-193). The purified protein appeared as a single band on a silver stain of an SDS-polyacrylamide gel electrophoresis. A given concentration of isolated plasminogen following activation with streptokinase demonstrated the predicted theoretical amidolytic activity, thereby confirming the purity of the isolated human plasminogen.

EXAMPLE 2

Iodination of plasminogen

Purified human plasminogen was iodinated by the chloramine T method using Iodobeads (Pierce Chem. Co., Rockford, Ill., U.S.A.) as described in Markwell, M. A. K., (1982) Anal. Biochem. 125:427-432. The labeled proteins were separated from free iodine by passage over a G-25 column (PD-10, Pharmacia) and collected in 0.15M Veronal buffered saline, pH 7.4, containing 0.001M $Mg^{2+}$, 0.00015M $Ca^{2+}$, and 0.1% gelatin (VBS-gel). The labeled proteins were stored in aliquots containing 0.02% sodium azide at $-20°$ C. The specific activity was approximately 25 mCi/mg. The concentration of $^{125}I$-plasminogen was determined using a modification of a previously described enzyme-linked immunosorbent assay (Reis, K. J., G. O. Von Mering, M. A. Karis, E. L. Faulmann, R. Lottenberg, and M. D. P. Boyle [1988] J. Immunol. Methods 107:273-280). The ELISA could accurately measure 1 ng/ml plasminogen.

EXAMPLE 3

Generation of plasmin

Plasmin was generated from radiolabeled plasminogen by incubation with urokinase (20 units/ml, Sigma Chemical Co., St. Louis, Mo., U.S.A.) in VBS-gel that contained 0.02M lysine. Conversion was maximal after 30 min at 37° C. The conversion of the single chain zymogen molecule to heavy and light chains was monitored, following reduction, on SDS-PAGE using the method of Laemmli as described previously (Lottenberg, R., C. C. Broder, M. D. P. Boyle [1987] Infect. Immmun. 55:1914-1918). Greater than 95% of plasminogen was consistently converted to plasmin. The specific activity of labeled plasmin was therefore essentially the same as labeled plasminogen.

EXAMPLE 4

Bacteria

The group A β-hemolytic streptococcal strain 64 had been previously subjected to mouse passage (Reis, K. J., M. Yarnall, E. M. Ayoub, M. D. P. Boyle [1984] Scand. J. Immunol. 20:433-439). The parent strain (64/P), as well as strains isolated after three (64/3) and fourteen (64/14) passages, were grown in Todd-Hewitt broth (DIFCO, Detroit, Mich.) overnight in phosphate-buffered saline (PBS), pH 7.4, containing 0.05% Tween-20 and 0.02% sodium azide. The bacteria were heat killed at 80° C. for 5 min, a treatment that did not alter their plasmin binding potential, but eliminated the production of soluble plasminogen activators which would interfere with these studies. The suspension was centrifuged, the pellet washed twice with PBS 0.02% sodium azide. Samples were stored at −20° C. The concentration of a bacterial suspension was determined by counting bacterial chains in a Neubauer hemacytometer (Fisher Scientific, Orlando, Fla., U.S.A.)

EXAMPLE 5

Effect of pH and ionic strength on binding

To assess the effect of pH on the bacterium: plasmin (ogen) interaction, 50 μl of labeled plasminogen of plasmin (approximately $2 \times 10^4$ cpm) were added to 1.0 ml of VBS containing 0.05% Tween-20 adjusted to the appropriate pH. After 15 min at room temperature, 50 μl of VBS containing approximately $10^7$ bacteria (strain 64/14) were added and the mixture was incubated at 37° C. for 15 min. The bacterial suspensions were centrifuged at 1000 g for 7 min to separate bacteria from unbound labeled proteins and the pellets were washed twice with 2 ml of VBS at the appropriate pH. The radioactivity associated with the bacterial pellet in duplicate experiments was measured using a Beckman 5500 autogamma counter.

Maximal binding of plasmin to the bacteria was observed between pH 5 and 8 with approximately 60% of counts offered being bound by the group A streptococcus 64/14. In contrast, addition of labeled plasminogen to the bacteria over the entire pH range tested (pH 5-9) resulted in direct binding of less than 10% of offered counts.

To assess the effect of ionic strength on the bacterium:plasmin (ogen) interaction, similar studies were carried out in solutions containing different concentrations of NaCl with 0.05% Tween-20. The bacterial pellets were washed in the appropriate NaCl concentration to remove unbound labeled proteins.

Plasmin binding was dependent on ionic strength and optimal binding occurred between 0.1 and 0.4M NaCl. In this range of salt concentrations, less than 10% of plasminogen bound to bacteria. As the ionic strength was lowered below 0.075M NaCl, significant binding of plasminogen to the bacteria was observed.

EXAMPLE 6

Effect of $Ca^{2+}$ and $Mg^{2+}$ on binding

Bindings of radiolabeled plasmin to group A streptococci strain 64/14 was studied in the following buffers: (1) VBS-gel containing 0.00015M $Ca^{2+}$ and 0.001M $Mg^{2+}$, or (2) metal free VBS-gel containing 0.15M ethylenediaminetetraacetic acid (EDTA). In each case 400 μl of buffer was added to 100 μl of VBS-gel containing approximately $10^7$ bacteria and 100 μl of VBS-gel containing $3 \times 10^4$ cpm of radiolabeled plasmin. After incubation at 37° C. for 15 minutes, the mixtures were centrifuged at 1000 g for 7 min to separate bacteria from unbound radiolabel, the pellets were washed twice with 2 ml of the appropriate buffer, and radioactivity associated with the bacterial pellet in duplicate experiments was measured.

The amount of plasmin bound by the bacteria was the same in the presence or absence of divalent cations.

EXAMPLE 7

Inhibition of binding by amino acids

Labeled plasmin (100 μl containing approximately $2 \times 10^4$ cpm) was added to 200 μl VBS-gel containing varying concentrations of epsilon-aminocaproic acid (EACA), lysine, or arginine, and incubated at 37° C. for 15 min. The pH of each solution was 7.0. One hundred μl of VBS-gel containing $10^7$ bacteria (strain 64/14) were then added and the mixture was incubated at 37° C. for 15 min. The bacterial suspensions were centrifuged at 1000 g for 7 min and washed twice with 2 ml of VBS-gel containing the same concentration of amino acid present during the incubation period. The percent inhibition of binding was calculated for duplicate experiments by comparison with binding in VBS-gel alone.

The ability of EACA, lysine, or arginine to dissociate bound plasmin from the bacteria was examined in the following manner. Labeled plasmin was incubated with $10^7$ bacteria in VBS-gel containing no amino acid at 37° C. for 15 min. The bacteria were pelleted by centrifugation and washed twice with 2 ml on VBS-gel. After determining the radioactivity associated with the bacteria, the pellets were resuspended in solutions of VBS-gel containing varying concentrations of amino acid (pH 7.0) as described above. The mixtures were incubated at 37° C. for 15 min and washed twice with VBS-gel containing the appropriate amino acid concentration. The radioactivity associated with the bacteria in duplicate experiments was again measured and the percentage dissociated was calculated.

Binding of plasmin to the group A streptococcus 64/14 was inhibited by each amino acid in a concentration dependent fashion. Fifty percent inhibition of binding of plasmin to the bacteria was observed at an EACA concentration of 0.15 mM a lysine concentration of 2.0 mM, and an arginine concentration of 25 mM. In similar studies, plasmin was prebound to the group A streptococcus and a concentration dependent elution of bound radiolabel was observed on incubation with EACA, lysine, or arginine. The concentration of amino acid required to elute 50% of the bound plasmin was approximately equivalent to that required to inhibit plasmin binding by 50%.

EXAMPLE 8

Determination of $K_D$ and receptor density

Labeled plasmin (25,000 to 250,000 cpm) in 100 μl of VBS-gel was added to $3 \times 10^6$ bacteria in 300 μl of VBS-gel, pH 7.4, and incubated at 37° C. for 15 min. The bacterial suspensions were centrifuged at 1000 g for 10 min and washed twice with 2 ml of VBS-gel. Experiments were performed in triplicate. Total binding was determined by measuring the radioactivity associated with the bacterial pellet when only labeled plasmin was offered. Non-specific binding was determined by preincubation bacteria at 37° C. for 15 min in VBS-gel, pH 7.4, containing unlabeled plasmin at a 100-fold molar excess of the labeled plasmin. Specific binding was calculated by subtracting non-specific binding from total binding for each amount of labeled plasmin offered. The amount of free labeled plasmin was calculated by subtracting the amount of specifically bound labeled plasmin from the total amount of labeled plasmin offered.

The apparent dissociation constant ($K_D$) was determined by two methods. A non-linear least squares analysis of the total counts offered vs. the counts bound fit to the simple Michaelis-Menten equation was performed (Cleland, W. W., [1967] Adv. Enzymol. 29:1-32). The concentration of plasmin was determined specific activity for the labeled plasminogen. Scatchard analysis (Scatchard, G., [1949] Ann. N.Y. Acad. Sci. 51:660-672) of these data was also performed. Counts bound vs. counts bound/counts free was plotted and the slope (representing $-1/K_D$) was determined by linear regression. The x-intercept (counts bound) was converted to moles of plasmin. Receptor density was calculated using this value and the number of bacterial chains offered (derived by hemacytometer chamber counts).

Plasmin which had been bound to and eluted form strain 64/14 by treatment with lysine was also examined in similar binding studies. Eluted plasmin was obtained by incubating 2 ml of stock 10% wet weight/volume bacterial suspension (strain 64/14) with approximately 20 μg of labeled plasmin at room temperature for 45 min. This suspension was centrifuged at 1000 g for 10 min and washed once with 10 ml of VBS-gel, and the radioactivity associated with the bacterial pellet was measured. The pellet was then resuspended in VBS-gel containing 20 mM lysine and incubated at room temperature for 30 min. The suspension was centrifuged and the supernatant recovered. Approximately 90% of the radioactivity originally associated with the bacterial pellet was dissociated by the lysine treatment. The dissociated plasmin in the supernatant was the subjected to gel filtration of a G-25 column to separate lysine from plasmin. Fractions containing plasmin were collected and stored at $-20°$ C.

Non-specific binding demonstrated a linear relationship to counts offered and was less than 5% in all tubes. Analysis of this data by least squares and Scatchard analysis demonstrated a $K_D$ of approximately $5 \times 10^{-11}$M for the association of plasmin with its receptor on the mouse passaged group A streptococcus strain 64/14. Scatchard analysis of the binding data indicates that there is a single population of plasmin receptors on streptococci, and that strain 64/14 possesses approximately 800 receptors per bacterium.

EXAMPLE 9

Dot-blotting Procedure for the Identification of Plasmin Receptor Activity

Bacterial extracts, chromatography fractions or standards were loaded into the wells of a dot-blotting manifold in 50-200 μl aliquots. Commercially available group C streptokinase was used as a positive plasmin binding control in each assay. All wells were washed twice with 200 μl aliquots of PBS-azide and vacuum drained. All samples were assayed in duplicate. Dot blots were blocked in 5.0 mM sodium diethylbarbiturate, 0.14M NaCl, 0.5% gelatin, 0.15% Tween 20, 0.004% $NaN_3$ pH 7.3. The blots were probed for 3-4 hours at room temperature in the blocking buffer containing 2.0 mM PMSF and $^{125}$I-labeled human plasmin at $3 \times 10^4$ cpm/ml. The probed blots were then washed in 0.01M EDTA pH 7.3, containing 0.5M NaCl 0.25% gelatin, 0.15% Tween 20, and 0.004% $NaN_3$. Autoradiographs were generated by exposing the nitrocellulose blots to Kodak XAR-5 film with an intensifying screen for 15-24 hours at $-70°$ C. followed by automated film developing.

EXAMPLE 10

Polyacrylamide Gel Electrophoresis and Protein Blotting

Gels intended for Western blotting were equilibrated in 25 mM Tris, 0.2M glycine pH 8.0 containing 20% v/v methanol (electroblot buffer) for 25 minutes. Protein blotting, from SDS-PAGE gels, was performed using the 'Trans-Blot SD Semi-Dry' electrophoretic transfer cell (Bio Rad, Richmond, Calif.). Blots were blocked as described for the dot-blot procedure, and probed for 3-4 hours at room temperature with radiolabeled human plasmin in either the presence or absence of 1.0 mM EACA, to identify functionally active protein bands. In studies of antigenic properties of these proteins, blots were probed with rabbit anti-plasmin receptor antibody or anti-group C streptokinase antibody by incubation with 4.3 μg IgG per ml of probing solution (approximately a 1:3000 dilution of antisera) for three hours and probed with $^{125}$I-streptococcal protein G containing $3 \times 10^4$ cpm/ml. For probing with mouse monoclonal antibodies specific for epitopes on group C streptokinase, blots were probed with a 1:100 dilution of the monoclonal antibody stock solution for three hours, followed by probing with goat antibody specific for mouse IgG at 1.0 μg/ml, followed by probing with $^{125}$I-streptococcal protein G containing $3 \times 10^4$ cpm/ml. Blots were then washed with 0.01M EDTA pH 7.3, containing 1.0M NaCl, 0.25% gelatin, 0.15% Tween 20. Autoradiographs were generated by exposing the nitrocellulose blots to Kodak XAR-5 film with an intensifying screen for 15-24 hours at $-70°$ C. followed by automated film developing.

EXAMPLE 11

Mutanolysin Extraction

Generation of cell membrane fragments of streptococcal cell strain 64/14 by mutanolysin generates functional plasmin receptor. Additional purification of receptor is accomplished by affinity chromatography with chemically modified plasmin (Broder et al.). The colony blot immunoassay to monitor the expression of Fc receptors on individual bacterial colonies is described in Yarnall, M., K. J. Reis, E. M. Ayoub, and M. D. P. Boyle (1984), "An immunoblotting technique for the detection of bound and secreted bacterial Fc receptors," J. Microbiol. Meth. 3:83-93.

This procedure is a modification of the method described by Yarnall, M. and M. D. P. Boyle. 1986) "Isolation and partial characterization of a type II Fc receptor from a group A streptococcus," Mol. Cell. Biochem. 70:57-66. Approximately 1.0 g wet weight of bacteria was suspended in 5.0 ml of 20 mM $KH_2PO_4$, 1.0 mM EDTA, 0.02% $NaN_3$ pH 7.0 containing 2.0 mM PMSF, 10 µg/ml DNAse I and 50 µg/ml mutanolysin. The suspension was vortexed and placed at 37° C. for 4 hours with periodic mixing. Supernatants were collected following centrifugation to remove bacteria and debris. For these studies a commercial preparation of mutanolysin was further purified according to the method described by Siegal et al. (Siegal, J. L., S. F. Hurst, E. S. Liberman, S. E. Coleman, and A. S. Bleiweis [1981] "Mutanolysin-induced spheroplasts of *Streptococcus mutans* are true protoplasts," Infect. Immun. 31:303-815) to remove contaminating protease.

EXAMPLE 12

Preparation of Immobilized Human Plasmin Affinity Support

Human plasminogen at a concentration of approximately $5.6 \times 10^{-5}$M was activated to plasmin by incubating the sample in the presence of an approximately 60 fold lower molar concentration of urokinase. The reaction was carried out with constant agitation for one hour at 37° C. in a reaction volume of 10 ml of 0.05M Tris, 0.15M NaCl pH 7.4 containing 40 mM lysine. A 50 µl aliquot was removed and analyzed by SDS-PAGE under reduced conditions to determine the extent of conversion of the single chain plasminogen molecule to the two chain plasmin form. The remainder of the reaction mixture was flash frozen, and stored at −70° C. Preparations in which complete conversion of plasminogen to plasmin was observed were then reacted with constant rotation with a 5 fold molar excess of D-valyl-L-phenylalanyl-L-lysine chloromethyl ketone at ambient temperature with constant rotation. The enzymatically inactive plasmin was then concentrated by ammonium sulfate precipitation (4.0 g/10 ml), dialyzed at 4° C. against 0.1M MOPS buffer, pH 7.3, containing 0.02% sodium azide. The dialyzed inactive plasmin was chromatographed on a Superose 6 column (Pharmacia, Piscataway, N.J.) in 0.1M MOPS buffer, pH 7.3.

The chlormethyl ketone blocked plasmin recovered from the molecular sieving column, was immobilized to the activated affinity chromatography support, Affi-Prep 10 (Bio Rad, Richmond, Calif.). This matrix couples in aqueous buffers to primary amino groups in the ligand by means of an N-hydroxysuccinimide ester on the end of a 10 carbon space arm. Approximately 50 mg of inactivated plasmin in 18 ml of 0.1M MOPS buffer, pH 7.3 was incubated with 6.0 ml of the Affi-Prep 10 bead suspension for 15 hours with rotation at 4° C. Following ligand coupling, 100 µl of 1.0M ethanolamine HCl pH 8 was added and the mixture rotated for 1 hour at 4° C. to block any remaining active sites on the Affi-Prep 10 matrix.

EXAMPLE 13

Affinity Purification of Plasmin Receptor

The Affi-Prep 10-Plasmin matrix was placed in an HR 10/10 column attached to a Pharmacia FPLC chromatography system. The column was equilibrated at room temperature in 0.05M $Na_2HPO_4$, 0.15M NaCl, 1.0 mM benzamidine HCl, 0.02% sodium azide pH 7.2 (equilibration buffer). Approximately 1 or 2 ml of supernatant from the mutanolysin extraction of bacterial strain 64/14 was loaded onto the column. The column was then washed with the equilibration buffer until the $OD_{280}$ returned to base line. The column was then eluted with a 50 ml linear gradient of 0.0M–0.1M L-Lysine in equilibration buffer, or eluted in a single step using equilibration buffer containing 0.1M L-Lysine. The absorbance at 280 nm was continuously monitored an 1.0 ml fractions were collected. After each affinity purification procedure the column was washed with 20 ml of 2.0M NaCl, followed by 200 ml of equilibration buffer and stored at 4° C.

EXAMPLE 14

Production of Polyclonal Antibodies to the extracted plasmin receptor in the mutanolysin extract of strain 64/14

Polyclonal antibodies to the $Mr \approx 41,000$ plasmin receptor protein extracted from strain 64/14 by mutanolysin extraction were prepared in both rabbits and mice. Rabbits were immunized with a gel slice from an SDS-polyacrylamide gel containing approximately 200 µg of the plasmin binding protein emulsified in Freund's complete adjuvant. The rabbit was boosted three times at two week intervals with a gel slice containing approximately 125 µg of the protein emulsified in Freund's incomplete adjuvant. The immunogen was prepared by separating the proteins in a mutanolysin extract of strain 64/14 by electrophoresis on 10% SDS-polyacrylamide gels. The gel was stained to identify protein bands. Plasmin binding proteins were identified by transferring the proteins in one lane of the gel to a nitrocellulose membrane and probing with $^{125}$I-labeled human plasmin, as described above.

Polyclonal antibodies to the $M_r \approx 41,000$ dalton plasmin binding protein were also prepared in mice. For these studies the immunogen was separated on 10% SDS-polyacrylamide gels under reducing conditions using a preparative comb with a single sample well. Separated proteins were transferred to nitrocellulose as described above. Functional plasmin binding proteins were identified by probing with $^{125}$I-labeled human plasmin. The remainder of the nitrocellulose sheet was then stained and the position of the 41,000 dalton band was located and aligned with the autoradiographed strip. The marked band on each nitrocellulose sheet was then carefully cut out to avoid any contamination, and divided into four equal fractions containing approximately 500 µg of protein. The strips were then equilibrated in PBS, sonicated to a fine powder, and subsequently mixed with Ribi Adjuvant. Aliquots of this mixture were used to immunize a group of 6-8 week old out-bred female mice as follows. Initially 10 mice were injected intraperitoneally with approximately 50 µg of antigen immobilized on the nitrocellulose membrane mixed with Ribi adjuvant. Two weeks after the initial injection the mice were boosted intraperitoneally with 10 µg of the nitrocellulose-bound antigen mixed with Ribi adjuvant. Four weeks after the initial injection, the mice were boosted intraperitoneally with 10 μg of nitrocellulose-bound antigen mixed with water. Four days after the final boost the mice were sacrificed and ascites fluid collected from each mouse, pooled and used as a source of antibody.

EXAMPLE 15

Solubility of Plasmin receptor

A variety of conditions for solubilizing plasmin receptor activity from the group A streptococcal strain 64/14 were compared. These included hot acid, alkaline, and neutral pH extractions, extraction with the detergents TRITON® X-100 with osmotic shock, acetone and TRITON® X-100 extraction, and extractions with the enzymes, lysozyme, trypsin, or mutanolysin. The highest yield of soluble plasmin binding activity was found in mutanolysin extracts.

The size heterogeneity of the soluble plasmin receptor activity in the mutanolysin extract of strain 64/14 was assessed by electrophoresis of a 50 μl aliquot of the extract on a series of parallel reducing or non-reducing SDS-polyacrylamide gels. The majority of the plasmin binding activity was present predominantly in a band with a Mr of approximately 41,000 daltons. One μg of purified group C streptokinase (Mr approx. 48,000 daltons) was electrophoresed as a positive control for plasmin binding. An aliquot of a sham mutanolysin digest, containing all the reactants, except the bacteria, was also analyzed by Western blotting techniques and demonstrated no plasmin binding activity (data not shown).

EXAMPLE 16

Relationship of the plasmin receptor to streptokinase

Although group A streptococcal plasmin receptor is functionally distinct from streptokinase, the release of this secreted plasmin (ogen) activator from strain 64/14, during extraction, would be a possible confusing factor in the isolation and characterization of the surface plasmin receptor.

The binding specificities of the plasmin receptor extracted from strain 64/14 with streptokinase present in the culture fluid of the same culture were compared. There was no plasminogen activator activity associated with any proteins in the extracted plasmin receptor preparation. A plasminogen activator activity at a $Mr \approx 48,000$ was seen in the lane containing the concentrated supernatant from strain 64/14. This protein migrated at a similar molecular weight in this gel system to the reference group C streptokinase protein.

Comparison of the ability of the samples to bind $^{125}$I-labeled human plasmin demonstrate that the $Mr \approx 48,000$ plasminogen activator bands associated with the reference group C streptokinase or the corresponding molecule from the concentrated culture supernatant of strain 64/14 bound the labeled probe. The mutanolysin extracted plasmin receptor displayed a $Mr \approx 41,000$ dalton band capable of binding to human plasmin; however, this molecule lacked any plasminogen activator potential. A minor $Mr \approx 41,000$ dalton band was present in the concentrated culture supernatant of strain 64/14 which also bound $^{125}$I-labeled human plasmin. This band displayed no plasminogen activator activity.

Previous studies have shown that the binding of human plasmin to the bacterial bound plasmin receptor on strain 64/14 could be inhibited in the presence of EACA. The plasmin binding activity of $Mr \approx 41,000$ dalton band present in the mutanolysin extract of strain 64/14 was reduced significantly in the presence of 1.0 mM EACA. Binding of $^{125}$I-labeled human plasmin to the $Mr \approx 41,000$ dalton plasmin binding protein in the concentrated culture supernatant of strain 64/14 was also inhibited by 1.0 mM EACA. By contrast, addition of EACA had no effect on the binding of plasmin to either the Mr 48,000 plasminogen activator protein from strain 64/14 or to the reference group C streptokinase molecule. Taken together these results indicate that the surface plasmin receptor solubilized by treatment of strain 64/14 with mutanolysin, was unrelated to the streptokinase protein secreted by the same organism. In addition, the results demonstrate that low levels of the plasmin receptor are found in bacterial free culture supernatants in which group A strain 64/14 was grown.

The mutanolysin extracted plasmin binding activity was subjected to further purification by affinity chromatography using an enzymatically inactivated plasmin affinity matrix prepared as described above. One ml of the mutanolysin extract of strain 64/14 was applied to the plasmin affinity column matrix in 0.05M Na$_2$HPO$_4$, 0.15M NaCl, 1.0 mM benzamidine HCl, and 0.02% NaN$_3$, pH 7.2. Bound plasmin receptor activity was eluted using a 50 ml linear gradient of 0.0–0.1M L-Lysine in 0.05M Na$_2$HPO$_4$, 0.15M NaCl, 1.0 mM benzamidine HCl, and 0.02% NaN$_3$, pH 7.2. The absorbance at 280 nm was monitored continuously and 1.0 ml fractions were collected. Fractions eluted from the affinity column were assayed for functional activity using a dot blotting procedure and $^{125}$I-labeled plasmin as the probe. The functional plasmin binding activity was found to bind to the immobilized plasmin matrix and could be eluted selectively with lysine. The recovered functional activity from the column corresponded to the eluted protein peak as detected by measuring absorbance at 280 nm. Identical results were obtained when a single concentration of 0.1M L-lysine was used to elute the bound plasmin receptor activity from the plasmin affinity column.

The molecular size and number of eluted proteins was determined by SDS-PAGE followed by silver staining. The functional activity eluted from the immobilized plasmin matrix in three 1.0 ml fractions. The greatest activity was found in the second protein containing fraction. Fifty microliters of this fraction was analyzed by Western blotting and probing with $^{125}$I-labeled human plasmin. The results indicated that a single $Mr \approx 41,000$ dalton protein was affinity purified and that this protein retained fractional plasmin binding activity. This protein corresponded to the activity present in the crude mutanolysin extract indicating that the affinity purification strategy did not result in any modification of the receptor.

Treatment of the affinity purified material with trypsin destroys the ability of the $Mr \approx 41,000$ dalton molecule to bind plasmin and results in the disappearance of this $Mr \approx 41,000$ dalton band on a silver stained SDS-polyacrylamide gel. These results indicate that a functionally active plasmin binding protein can be isolated by affinity chromatography for a mutanolysin extract of the group A streptococcal strain 64/14. The affinity purified protein, like the crude extract, lacked any plasminogen activating potential.

The group A streptococcal plasmin receptor and streptokinase are physicochemically and functionally distinct molecules. The possibility that the two proteins arose from a common precursor and shared at least some antigenic determinants was considered. This possibility was examined using a polyclonal antibody to streptokinase, as well as rabbit and mouse polyclonal antibodies prepared against the plasmin receptor isolated from strain 64/14.

These findings indicate that the plasminogen activator proteins secreted by group A and group C streptococci were antigenically related. By contrast the $Mr \approx 41,000$ plasmin binding protein extracted from the bacteria or present in low concentrations in culture supernatants displayed no antigenic relatedness with streptokinase as detected by the monospecific polyclonal antibody used.

By contrast, the group A plasmin receptor protein solubilized from the 64/14 bacterial surface was totally devoid of any of the antigenic determinants detected by this the polyclonal anti-streptokinase antibody.

EXAMPLE 17

A portion of the amino acid sequence of the novel plasmin receptor has now been determined. The 70 amino acids at the amino terminus of the protein are as follows:

| 1   |     |     |     | 5   |     |     |     |     | 10  |
|-----|-----|-----|-----|-----|-----|-----|-----|-----|-----|
| Val | Val | Lys | Val | Gly | Ile | Asn | Gly | Phe | Gly |
| Arg | Ile | Gly | Arg | Leu | Ala | Phe | Arg | Arg | Ile |
| Gln | Asn | Ile | Glu | Gly | Val | Glu | Val | Thr | Arg |
| Ile | Asn | Asp | Leu | Thr | Asp | Pro | Asn | Met | Leu |
| Ala | His | Leu | Leu | Lys | Tyr | Asp | Thr | Thr | Gln |
| Gly | Arg | Phe | Asp | Gly | Thr | Val | Glu | Val | Lys |
| Glu | Gly | Gly | Phe | Glu | Val | Asn | Gly | Asn | Phe |

This sequence can be used to confirm identification of this receptor molecule and other related receptor molecules. Also, this region may have important binding properties.

As described below, clones comprising DNA coding for the amino acid sequence of the receptor have been identified. Also, DNA encoding this amino acid sequence can be synthesized using procedures well known to those skilled in the art. DNA encoding all or part of the receptor are useful for producing the receptor and for screening DNA libraries of other bacteria in order to identify analogous receptor proteins. Also, fragments of the receptor protein can be produced for use in determining the region(s) of the protein responsible for the binding of the plasmin or for the inhibition of $\alpha 2$ antiplasmin activity.

EXAMPLE 18

As described above, the protein responsible for plasmin binding has been purified from group A streptococcal strain 64/14 and is functionally and antigenically distinct from the plasminogen activator, streptokinase, isolated from the same strain. A genomic library was constructed in lambda gt11 from group A streptococcus strain 64/14. Approximately 13,000 plaques were screened for reactivity to polyclonal antiserum against the isolated plasmin receptor. The protein products of three positive clones were subjected to SDS-polyacrylamide gel electrophoresis and Western blot analysis. These clones produced an immunoreactive protein with an apparent Mr identical to the streptococcal receptor (41 Kd). A casein-agarose underlay assay revealed plasmin-binding activity for the cloned products.

The clones have been transformed into and expressed in *E. coli*. *E. coli* hosts containing the clones will be deposited into the permanent collection of the American Type Culture Collection (ATCC), 12301 Parklawn Drive, Rockville, Md. 20852 USA. The cultures will be assigned accession numbers by the repository.

The subject cultures will be deposited under conditions that assure that access to the cultures will be available during the pendency of this patent application to one determined by the Commissioner of Patents and Trademarks to be entitled thereto under 37 CFR 1.14 and 35 USC 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit(s), and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

EXAMPLE 19

Clinical use of bacterial plasmin receptors

The plasmin receptors described above can be either purified from bacteria or produced by recombinant technology. These receptors bind plasmin with high affinity but the plasmin retains enzymatic activity. Although plasmin is normally inhibited rapidly by $\alpha 2$ antiplasmin, such inhibition occurs more slowly and to a lesser extent when plasmin is bound to the receptor. These characteristics of the receptor and the plasmin bound to the receptor suggest several novel methods for thrombolytic therapy. First, a composition comprising the purified receptor can be administered in combination with the administration of a plasminogen activator. The receptor may be administered concurrently with the administration of the plasminogen activator. Alternatively, the compositions may be administered sequentially. The receptor should be administered before plasmin produced by the activity of the plasminogen activator has been substantially inhibited by $\alpha 2$ antiplasmin. Therefore, for best results the receptor should be administered concurrently with, or shortly before or after, the administration of the plasminogen activator. This procedure has the advantage of decreasing the amount and frequency of administration of the plasminogen activator. Normally, the short half life of TPA necessitates frequent administration of that agent. Also, the administration of TPA or other plasminogen activators can result in substantial amounts of freely circulating plasmin. This situation is most likely to occur with plasminogen activators such as streptokinase, which do not have any particular affinity for fibrin. A reduction in free plasmin is important to minimize the possibility of unwanted bleeding. Also, it is believed that under some circumstances free plasmin can actually lead to more fibrin deposition and it may also be detrimental to platelet function.

In a further embodiment, the receptor can be bound to plasmin before administration to the human or animal in need of treatment. When the receptor is bound to plasmin the receptor/plasmin complex can then be administered to a human or animal in need of fibrinolytic activity. The plasmin would then supply this activity without being rapidly inhibited by α2 antiplasmin. This procedure also decreases the amount and frequency of administration of the therapeutic agent.

A further advantage of administering plasmin receptor or plasmin bound to a receptor is that the host's plasminogen is not depleted as much as when plasminogen activators alone are administered. When plasminogen activators alone are administered, much of the plasmin is not specifically directed to the desired location and it simply becomes inactivated through the action of α2-antiplasmin. When the plasmin receptor is administered in combination with the plasminogen activator, it is not necessary to use as much activator and, consequently, the host's plasminogen is conserved. Also, administration of the receptor-plasmin complex provides the host with a source of fibrinolytic activity without depleting the host's own plasminogen.

A further embodiment of the subject invention comprises the conjugation of the receptor or a receptor-plasmin complex to an antibody for fibrin. Antibodies to fibrin are known to those skilled in the art and can be easily produced by those skilled in the art. It is a straightforward matter to a person skilled in the art to conjugate the receptor or receptor-plasmin complex to an appropriate anti-fibrin antibody. The resulting conjugate then directs the fibrinolytic activity of the bound plasmin to the specific site where the activity is needed.

An alternative therapeutic procedure comprises the administration of plasmin bound to inactivated bacteria. In this embodiment the receptor remains attached to the bacteria and the plasmin then binds to the essentially immobilized receptor. Heat-treated or otherwise inactivated bacteria can be prepared in a sterile manner. Human plasminogen (pyrogen and microbial organism-free) can be converted to active plasmin using urokinase under conditions previously described (Lottenberg, R., F. R. Dolly, and C. S. Kitchens [1985] Am. J. Hematology 19:181-193). Incubation of the bacteria and plasmin to allow complex formation can be followed by washing of the bacteria to remove unbound plasmin. Streptococcal strains non-pathogenic for humans expressing high levels of plasmin receptors provide an example of bacteria which can be used in the novel process disclosed here. Alternative strains of bacteria or other microorganisms, such as fungi, can also be used. Streptococci expressing fibrinogen receptor, in addition to the plasmin receptor, may offer enhanced fibrin specificity in that the fibrinogen receptor binds to fibrin (ogen). For strains of streptococci harboring a fibrinogen binding component, cell membrane fragments containing this region may provide enhanced fibrin specificity. Advantageously, bacteria with associated plasmin may become entrapped by the thrombus. The enzymatic activity of the plasmin would provide for fibrin degradation leading to thrombus dissolution. Clearance of unassociated bacterium-plasmin conjugates by the reticulo-endothelial system would remove the bacteria from circulation.

Anticipated applications of combination therapies or bacterium-plasmin conjugates as thrombolytic agents in clinical practice include intravenous administration for pulmonary thromboembolism, venous thrombosis, acute myocardial infarction, and local infusion for acute arterial thrombosis, and catheter or other intravascular device occlusion. These treatments essentially target the fibrinolytic activity to the specific location where it is needed. Thus, it is not necessary to provide high level systemic dosages. As described above, one preferred embodiment of the invention involves the combined use of the novel receptor-plasmin conjugates with other available treatments. Such a combination can be used to take advantage of the targeted action of the conjugate as well as the more generalized lytic state resulting from the administration of thrombolytic agents. The deleterious side effects normally associated with the thrombolytic agent can be minimized because lower concentrations are needed when they are administered in conjunction with the immobilized plasmin.

An additional aspect of controlling potential hemorrhagin accompanying administration of this agent may be the intravenous administration of epsilonaminocaproic acid (tradename AMICAR) or tranexamic acid. Typical regimens of these anti-fibrinolytic agents would provide plasma levels of the lysine analogs to dissociate the plasmin from the bacteria (Broeseker, T. A., M. D. P. Boyle and R. Lottenberg [1988] "Characterization of the interaction of human plasmin with its specific receptor on a group A streptococcus", Microbial Pathogenesis 5:19-27) and enable rapid inactivation of plasmin by its physiological inhibitors α2-antiplasmin and α2-macroglobulin. This will also provide an approach to prepare the patient for emergency surgical procedures (e.g., coronary artery bypass grafting or administration of alternating anti-thrombotic agents (e.g., heparin).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated plasmin receptor which is a surface protein obtainable from Group A streptococci and which comprises an amino terminus as follows:

| Val | Val | Lys | Val | Gly | Ile | Asn | Gly | Phe | Gly |
|-----|-----|-----|-----|-----|-----|-----|-----|-----|-----|
| Arg | Ile | Gly | Arg | Leu | Ala | Phe | Arg | Arg | Ile |
| Gln | Asn | Ile | Glu | Gly | Val | Glu | Val | Thr | Arg |
| Ile | Asn | Asp | Leu | Thr | Asp | Pro | Asn | Met | Leu |
| Ala | His | Leu | Leu | Lys | Tyr | Asp | Thr | Thr | Gln |
| Gly | Arg | Phe | Asp | Gly | Thr | Val | Glu | Val | Lys |
| Glu | Gly | Gly | Phe | Glu | Val | Asn | Gly | Asn | Phe. |

2. A protein conjugate, comprising said plasmin receptor of claim 1, conjugated to an anti-fibrin antibody.

3. A protein conjugate, comprising said plasmin receptor of claim 1, bound to plasmin.

* * * * *

UNITED STATES PATENT AND TRADEMARK OFFICE
CERTIFICATE OF CORRECTION

PATENT NO. : 5,237,050

DATED : August 17, 1993

INVENTOR(S) : Michael D.P. Boyle, Richard Lottenberg, Christopher Broder and Gregory Von Mering It is certified that error appears in the above-identified patent and that said Letters Patent is hereby corrected as shown below:

Column 2     line 53: Delete "human nad" and insert --human and--.

Column 3     line 51: Delete "of teh oirganisms" and insert --of the organisms--.

Column 9     line 66: Delete "and the mixture" and insert --and the reaction mixture--.

Signed and Sealed this

Twenty-second Day of March, 1994

Attest:

BRUCE LEHMAN

Attesting Officer     Commissioner of Patents and Trademarks